(12) United States Patent
Lundgren-Åkerlund

(10) Patent No.: US 8,105,791 B2
(45) Date of Patent: Jan. 31, 2012

(54) MARKER FOR STEM CELLS AND ITS USE

(75) Inventor: Evy Lundgren-Åkerlund, Bjarred (SE)

(73) Assignee: Xintela AB, Bjarred (SE)

( * ) Notice: Subject to any disclaimer, the term of this patent is extended or adjusted under 35 U.S.C. 154(b) by 0 days.

(21) Appl. No.: 12/787,224

(22) Filed: May 25, 2010

(65) Prior Publication Data

US 2011/0033923 A1    Feb. 10, 2011

Related U.S. Application Data

(62) Division of application No. 10/517,210, filed as application No. PCT/SE03/00983 on Jun. 12, 2003, now Pat. No. 7,749,710.

(60) Provisional application No. 60/388,298, filed on Jun. 14, 2002.

(30) Foreign Application Priority Data

Jun. 14, 2002 (SE) .................................. 0201831

(51) Int. Cl.
 *G01N 33/53* (2006.01)
(52) U.S. Cl. ........................................ 435/7.1; 435/7.21
(58) Field of Classification Search .................. None
 See application file for complete search history.

*Primary Examiner* — Maher Haddad
(74) *Attorney, Agent, or Firm* — Finnegan, Henderson, Farabow, Garrett & Dunner, LLP

(57) ABSTRACT

A marker for mesenchymal stem cells (MSC) is provided, comprising an integrin alpha10 chain and/or an integrin alpha11 chain expressed on the cell surface of or intracellular in a MSC. The marker is used in methods for identification of mammalian MSC and in methods for isolation of MSC. Also included are isolated cellular populations of mammalian MSC and a cellular composition comprising the latter. Moreover, uses of said marker for isolation, modulation and identification of mammalian MSC are provided.

5 Claims, 4 Drawing Sheets

SEQUENCE LISTING

```
<160> NUMBER OF SEQ ID NOS: 10

<210> SEQ ID NO 1
<211> LENGTH: 7
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Variable amino acid
<220> FEATURE:
<221> NAME/KEY: MISC_FEATURE
<222> LOCATION: (6)..(6)
<223> OTHER INFORMATION: Arginine or Lysine

<400> SEQUENCE: 1

Lys Xaa Gly Phe Phe Xaa Arg
1               5

<210> SEQ ID NO 2
<211> LENGTH: 7
<212> TYPE: PRT
<213> ORGANISM: Homo sapiens

<400> SEQUENCE: 2

Lys Leu Gly Phe Phe Ala His
1               5

<210> SEQ ID NO 3
<211> LENGTH: 5
<212> TYPE: PRT
<213> ORGANISM: Homo sapiens

<400> SEQUENCE: 3

Gly Phe Phe Lys Arg
1               5

<210> SEQ ID NO 4
<211> LENGTH: 5
<212> TYPE: PRT
<213> ORGANISM: Homo sapiens

<400> SEQUENCE: 4

Phe Gly Gly Ala Pro
1               5

<210> SEQ ID NO 5
<211> LENGTH: 5
```

-continued

```
<212> TYPE: PRT
<213> ORGANISM: Homo sapiens

<400> SEQUENCE: 5

Met Ile Asp Ala Ser
1               5

<210> SEQ ID NO 6
<211> LENGTH: 5
<212> TYPE: PRT
<213> ORGANISM: Homo sapiens

<400> SEQUENCE: 6

Gly Phe Phe Arg Ser
1               5

<210> SEQ ID NO 7
<211> LENGTH: 23
<212> TYPE: DNA
<213> ORGANISM: Artificial Sequence
<220> FEATURE:
<223> OTHER INFORMATION: Forward PCR primer for integrin alpha 10

<400> SEQUENCE: 7
gctccaggaa ggccccattt gtg                                          23

<210> SEQ ID NO 8
<211> LENGTH: 24
<212> TYPE: DNA
<213> ORGANISM: Artificial Sequence
<220> FEATURE:
<223> OTHER INFORMATION: Reverse PCR primer for integrin alpha 10

<400> SEQUENCE: 8
gtgttttctt gaagggtgcc attt                                         24

<210> SEQ ID NO 9
<211> LENGTH: 19
<212> TYPE: DNA
<213> ORGANISM: Artificial Sequence
<220> FEATURE:
<223> OTHER INFORMATION: Forward PCR primer for integrin alpha 11

<400> SEQUENCE: 9
gctgcaggca gtgacagta                                               19

<210> SEQ ID NO 10
<211> LENGTH: 19
<212> TYPE: DNA
<213> ORGANISM: Artificial Sequence
<220> FEATURE:
<223> OTHER INFORMATION: Reverse PCR primer for integrin alpha 11

<400> SEQUENCE: 10
gcgatgggaa tggtgatct                                               19
```

MARKER FOR STEM CELLS AND ITS USE

This is a divisional application of U.S. application Ser. No. 10/517,210, filed Mar. 9, 2005, now U.S. Pat. No. 7,749,710, issued Jul. 6, 2010, which is a National Stage Entry of PCT International Application No. PCT/SE03/00983, filed Jun. 12, 2003, which claims the benefit of priority of Swedish Application No. 0201831-5, filed Jun. 14, 2002, and of U.S. Provisional Application No. 60/388,298, filed Jun. 14, 2002. All of the above listed applications are hereby incorporated by reference in their entirety.

TECHNICAL FIELD

This invention relates to a marker for isolation and identification of mammalian mesenchymal stem cells. Also included are methods and uses of such a marker as well as an enriched cellular population and a cellular composition comprising the enriched cellular composition.

BACKGROUND OF THE INVENTION

Mesenchymal Stem Cells

Figure 1:
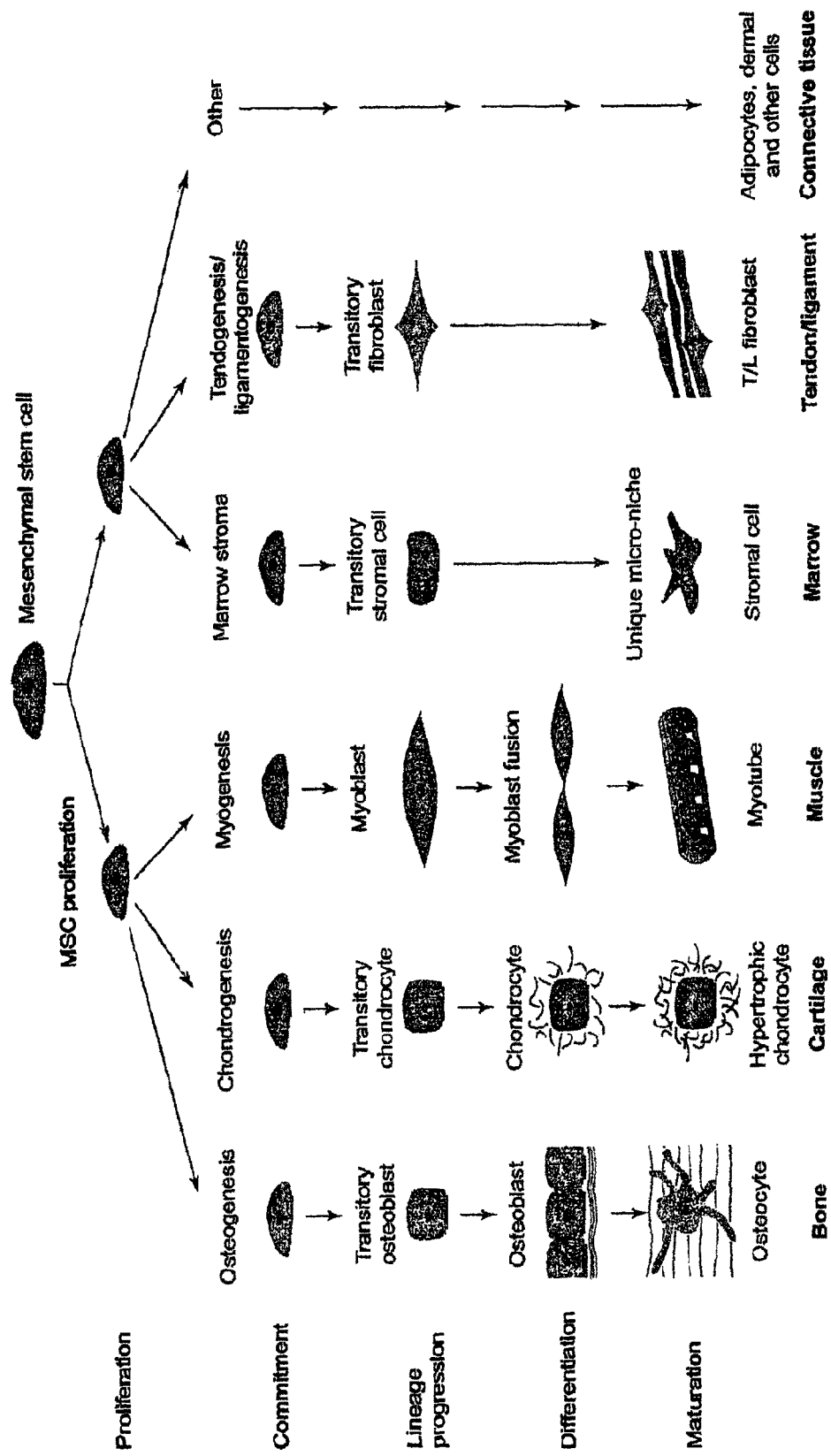

The adult body houses so called stem cells that are capable of dividing many times while also giving rise to daughter cells with specific phenotypical characteristics. Several types of stem cells exist in the body including embryonic stem cells, haematopoietic stem cells and mesenchymal stem cells. Mesenchymal stem cells are able to form mesenchymal tissues such as bone, cartilage, muscle, bone, ligament, fat and bone marrow stroma. FIG. 1 shows a schedule of suggested stepwise transitions from putative mesenchymal stem cells (MSC) to highly differentiated phenotypes. The mesenchymal stem cells are located in bone marrow, around blood vessels, in fat, skin, muscle, bone and other tissues. Their presence contributes to the reparative capacity of these tissues.

Medical use of MSC

Currently, the medical use of MSC is to explore their potential in the regeneration of tissues that the body cannot naturally repair or regenerate when challenged. For this, MSC, are isolated, expanded in culture and stimulated to differentiate into connective tissues such as bone, cartilage, muscle, bone marrow stroma, tendon, fat and others. These tissue-engineered constructs can then be re-introduced into the human body to repair lost or damaged tissue. In another approach MSC can be directly stimulated in vivo to induce the formation of specific tissues in situ.

Having defined MSC as potential "building blocks" for tissue engineering and transplantation, researchers are now searching for better ways to identify, isolate and characterize MSC.

Alpha10

A newly discovered collagen-binding integrin, alpha10beta1, includes the integrin subunit alpha10 (Camper et al., (1998) J. Biol. Chem. 273:20383-20389). The integrin is expressed on chondrocytes and shows a $M_r$ of 160 kDa after reduction when isolated from bovine chondrocytes by collagen type II affinity purification.

Cloning and cDNA sequencing showed that it shares the general structure of other integrin alpha subunits. The predicted amino acid sequence consists of a 1167-amino acid mature protein, including a signal peptide (22 amino acids), a long extracellular domain (1098 amino acids) a transmembrane domain (22 amino acids), and a short cytoplasmic domain (22 amino acids). In contrast to most alpha-integrin subunits, the cytoplasmic domain of alpha10 does not contain the conserved sequence KXGFF(R/K)R (SEQ ID NO: 1). Instead, the predicted amino acid sequence in alpha10 is KLGFFAH (SEQ ID NO: 2). It is suggested that the GFFKR (SEQ ID NO: 3) motif in alpha-chains are important for association of integrin subunits and for transport of the integrin to the plasma membrane (De Melker et al. (1997) Biochem. J. 328:529-537).

The extracellular part contains a 7-fold repeated sequence, an I-domain (199 amino acids) and three putative divalent cation-binding site. Sequence analysis has revealed that the alpha10 subunit is most closely related to the I domain-containing α subunits with the highest identity to alpha1 (37%), alpha2 (35%) and alpha11 (42%).

Alpha11

The alpha11 integrin has recently been identified and cloning and characterisation revealed an I-domain containing, beta1-associated integrin.

The open reading frame of the cDNA encodes a precursor of 1188 amino acids. The predicted mature protein of 1166 amino acids contains 7 conserved FGGAP (SEQ ID NO: 4) repeats, an I-domain with a MIDAS (SEQ ID NO: 5) motif, a short transmembrane region and a unique cytoplasmic domain of 24 amino acids containing the sequence GFFRS (SEQ ID NO: 6).

Alpha11 contains three potential divalent cation binding sites in repeats 5-7. The presence of 22 inserted amino acids in the extracellular stalk portion (amino acids 804-826) distinguishes the alpha11 integrin sequence further from other integrin alpha-chains.

Amino acid sequence comparisons reveal the highest identity (42%) with the alpha10 integrin chain. Immunoprecipitation with antibodies to the alpha11 integrin captured a 145 kDa protein, distinctly larger than the 140 kDa alpha2 integrin chain when analysed by SDS-PAGE under non-reducing conditions.

Isolation and Identification of MSC

The identification of MSC in situ is hampered by the fact that mono-specific and unique molecular probes do not exist. It is therefore necessary to further characterize mesenchymal stem cells to identify probes or combinations of probes that can unequivocally identify mesenchymal stem cells in tissue. Such markers will also be useful for the isolation of mesenchymal stem cells from bone marrow (BM) and blood tissues.

Approximately one cell out of 10.000-100.000 nucleated cells in bone marrow aspirates is expected to be a mesenchymal stem cell. Currently, the main method for the isolation of mesenchymal stem cells from bone marrow is based on their capacity to adhere to plastic culture dishes and form colonies while the majority of bone marrow cells do not adhere and form colonies. These colonies are then further expanded and then induced with defined factors to differentiate into specific mesenchymal tissues. It is not clear, however, whether the mesenchymal stem cells isolated this way are a homogenous population. It will therefore be important to find markers that can be used to identify subclasses of mesenchymal stem cells with specific differentiation potentials.

In U.S. Pat. No. 6,200,606, the isolation of cartilage or bone precursor cells from haematopoietic and non-haematopoietic cells by the use of CD34 as a negative selection marker and the further use of isolated stem cells in bone and cartilage regeneration processes is described. Still, no specific marker for mesenchymal stem cells is identified nor disclosed. The CD34 marker is expressed on early lymphohaematopoietic stem and progenitor cells, small-vessel endothelial cells, embryonic fibroblasts, and some cells in foetal and adult nervous tissue, haematopoietic progenitors derived from foetal yolk sac, embryonic liver, and extra-hepatic embryonic tissues including aorta-associated haematopoietic progenitors in the 5 week human embryo.

Pittenger at al. ((1999) Science 284:143-147) have used a density centrifugation of human bone marrow to isolate human MSC. Cellular markers used to identify the MSC are SH-2, SH-3, CD29, CD44, CD71, CD90, CD106, CD120a, CD124.

Majumdar et al., ((2000) J. Cell. Physiol. 185:98-106) have used CD105 as a marker for enrichment of human MSC from bone marrow.

Denni et al., ((2002) Cells Tissues Organs 170:73-82) have used a marker called Stro-1 to enrich human MSC from bone marrow.

All markers mentioned so far may be used for enrichment of hMSC. Still, they are not exclusive for MSC, the isolated population is heterogenous when enriched using these markers. Monospecific and unique probes for the identification of hMSC do not exist as of today.

Furthermore, markers are needed to monitor the differentiation of mesenchymal stem cells into specific types of mesenchymal cells. This will be especially important when these cells are re-introduced into the human body to replace loss of damaged mesenchymal tissue, such as bone or cartilage.

Finally, the identification of specific cell surface markers for mesenchymal stem cells may be used for their isolation out of a complex mixture of cells by cell sorting techniques such as fluorescence activated cell sorting (FACS).

It is thus highly desirable in the light of the aforementioned problems to identify and isolate MSC, for further use in bone, cartilage, muscle, bone marrow, tendon or connective tissue repair in vivo or in vitro. In this respect, the present invention addresses this needs and interest.

SUMMARY OF THE INVENTION

In view of the foregoing disadvantages known in the art when trying to isolate and identify mammalian MSC, the present invention provides marker for mammalian MSC suitable for identifying and isolating mammalian MSC.

One object with the present invention is to provide methods for identifying, or isolating mammalian MSC, or an enriched cellular population of MSC.

Another object is to provide uses of the marker according to the invention for identifying or isolating mammalian MSC.

Thus, the present invention provides a marker for mammalian mesenchymal stem cells. The marker comprises an integrin alpha 10 chain and/or integrin alpha 11 chain expressed on the cell surface of mesenchymal stem cell or intracellular in a mesenchymal stem cell.

Further embodiments include wherein the integrin alpha10 and/or integrin alpha 11 chain is expressed as a heterodimer in combination with an integrin beta1 chain.

Also, the present invention provides a method for identifying a mammalian mesenchymal stem cell. Such a method comprises the steps of
a) providing a sample comprising a mesenchymal stem cell,
b) detecting integrin alpha10 and/or alpha11 chain expression on the cell surface of a mesenchymal stem cell or intracellular in a mesenchymal stem cell,
c) scoring the integrin alpha10 and/or alpha11 chain expression, and
d) identifying the mesenchymal stem cell according to the scoring in c) above.

Further embodiments include wherein the expression in b) above is detected by detecting the integrin alpha10 and/or integrin alpha 11 protein expression.

Even further embodiments include wherein the expression in b) above is detected by detecting the integrin alpha10 and/or integrin alpha 11 mRNA expression.

Even further, the present invention provides a method for determining whether a test compound modulates a mammalian mesenchymal stem cell differentiation.
Such a method comprises the steps of
a) providing a mesenchymal stem cell
b) contacting the mesenchymal stem cell with a test compound, and
c) detecting a change in rate or pattern of differentiation of the mesenchymal stem cell as an indication of that the test compound modulates mesenchymal stem cell differentiation.

Still even further, the present invention provides a method for producing an isolated population of mammalian cells enriched for mesenchymal stem cells relative a reference population. Such a method comprises the steps of
a) providing at least a portion of a population of cells, or a portion of a reference population, comprising MSC and at least one cell other than the mesenchymal stem cells,
b) introducing into the population of cells in a) above a compound identifying the mesenchymal stem cells,
c) selecting and isolating from the population of cells in b) above the mesenchymal stem cells, thereby producing a population of cells enriched for mesenchymal stem cells.

The method according to the invention may in further embodiments include wherein the mesenchymal stem cells is identified as a mesenchymal stem cell by detecting expression of integrin alpha10 and/or alpha11 chain expression on the cell surface of said mesenchymal stem cells according to the method disclosed in the present invention.

Even further, an enriched mammalian cellular population of mesenchymal stem cells, comprising at least one intact, viable mesenchymal stem cell is disclosed. Such enriched cellular population is a population wherein the mesenchymal stem cell is characterised by
a) expressing an integrin alpha 10 chain and/or integrin alpha 11 chain on the cell surface of or intracellular in said mesenchymal stem cell,
b) being substantially free from expression of molecules specific for committed lymphohaematopoietic cells or uncommitted stem cells.

Also, an isolated mammalian mesenchymal stem cell expressing a marker according to the invention, obtainable by the method for producing a population of cells enriched for mesenchymal stem cells according to the invention is disclosed.

Still even further, a mammalian cellular composition comprising the enriched cellular population according to the invention, or the isolated mesenchymal stem cell according to the invention is disclosed.

Uses of a marker according to the invention for identification of a mammalian mesenchymal stem cell, for modulating differentiation of a mammalian mesenchymal stem cell and for isolating a mammalian mesenchymal stem cell are also provided.

SHORT DESCRIPTION OF DRAWINGS

FIG. 1 shows a schematic view of a suggested stepwise transition from putative mesenchymal stem cell (MSC) to highly differentiated phenotypes. (From Caplan A. I. and Bruder S. P Trends Mol. Med. 2001, 7(6): 259-264).

Figure 2:
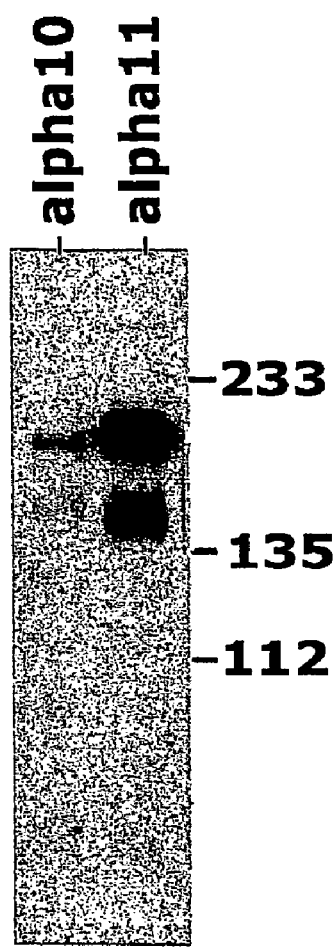

FIG. 2 shows that human mesenchymal stem cells in culture express both integrin alpha10 and alpha11 chains on their cell surface. In the figure, the upper band in both lanes is alpha10 (in the left lane) and alpha11 (in the right lane). The lower band in both lanes represents the beta1 chain.

Figure 3:
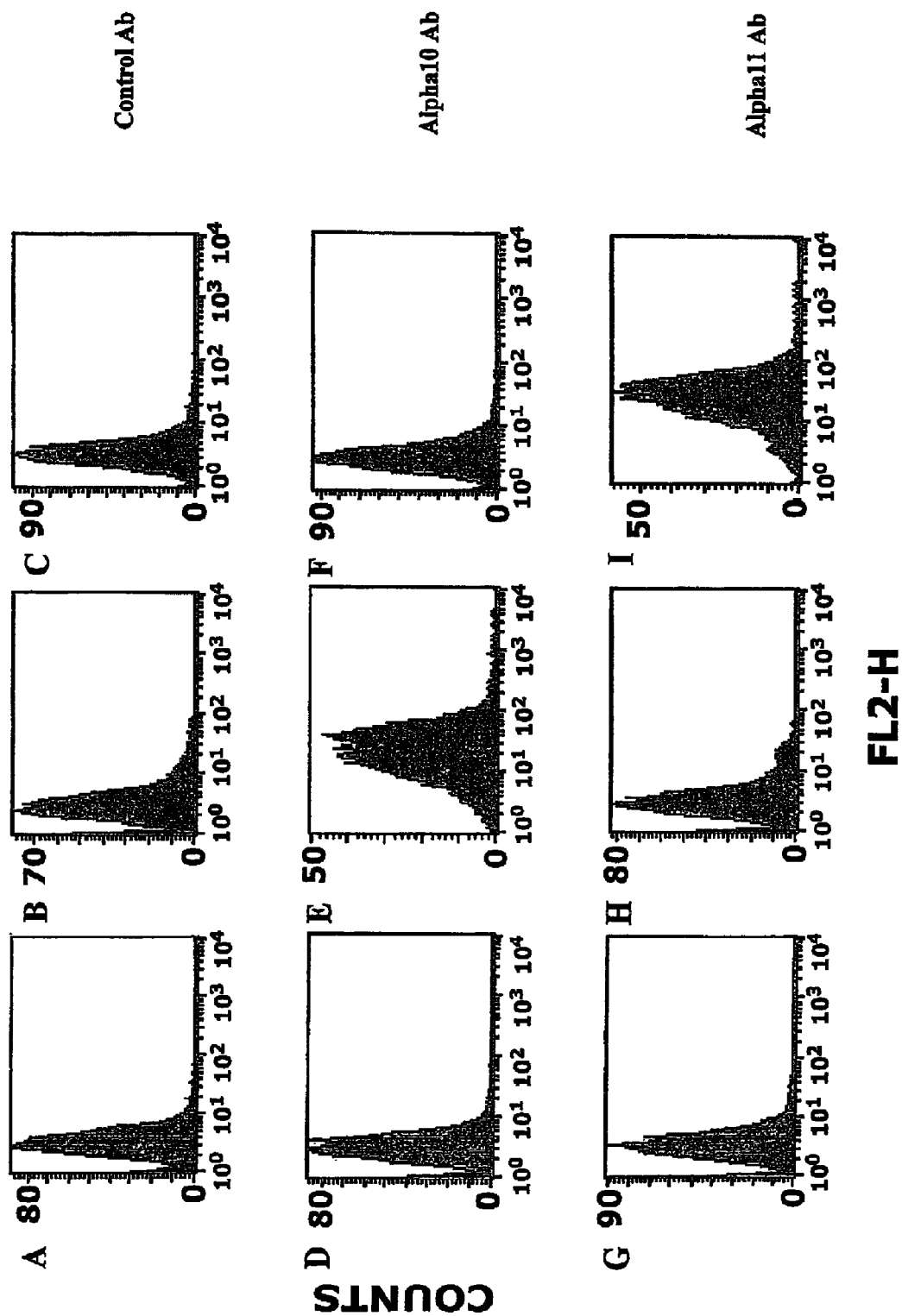

FIG. 3 shows histograms after flow cytometry analysis. Shown in FIG. 3E the antibody against alpha10 bound to the HEK293 cells transfected with human alpha10 integrin-subunit is seen. The antibody against alpha10 did not bind to HEK293 cells tranfected with human alpha11 integrin-subunit, as shown in the middle panel (right, FIG. 3F), or untranfected HEK293 cells, as shown in FIG. 3D). Shown in FIG. 3I, the antibody against alpha11 bound to the HEK293 cells transfected with human alpha11 integrin-subunit. The antibody against alpha11 did not bind to HEK293 cells transfected with human alpha10 integrin-subunit, as shown in FIG. 3H, or untransfected HEK293 cells, as shown in FIG. 3G). FIG. 3A-C represent control (secondary antibody alone), which did not bind to any of the HEK293 cells tested.

Figure 4:
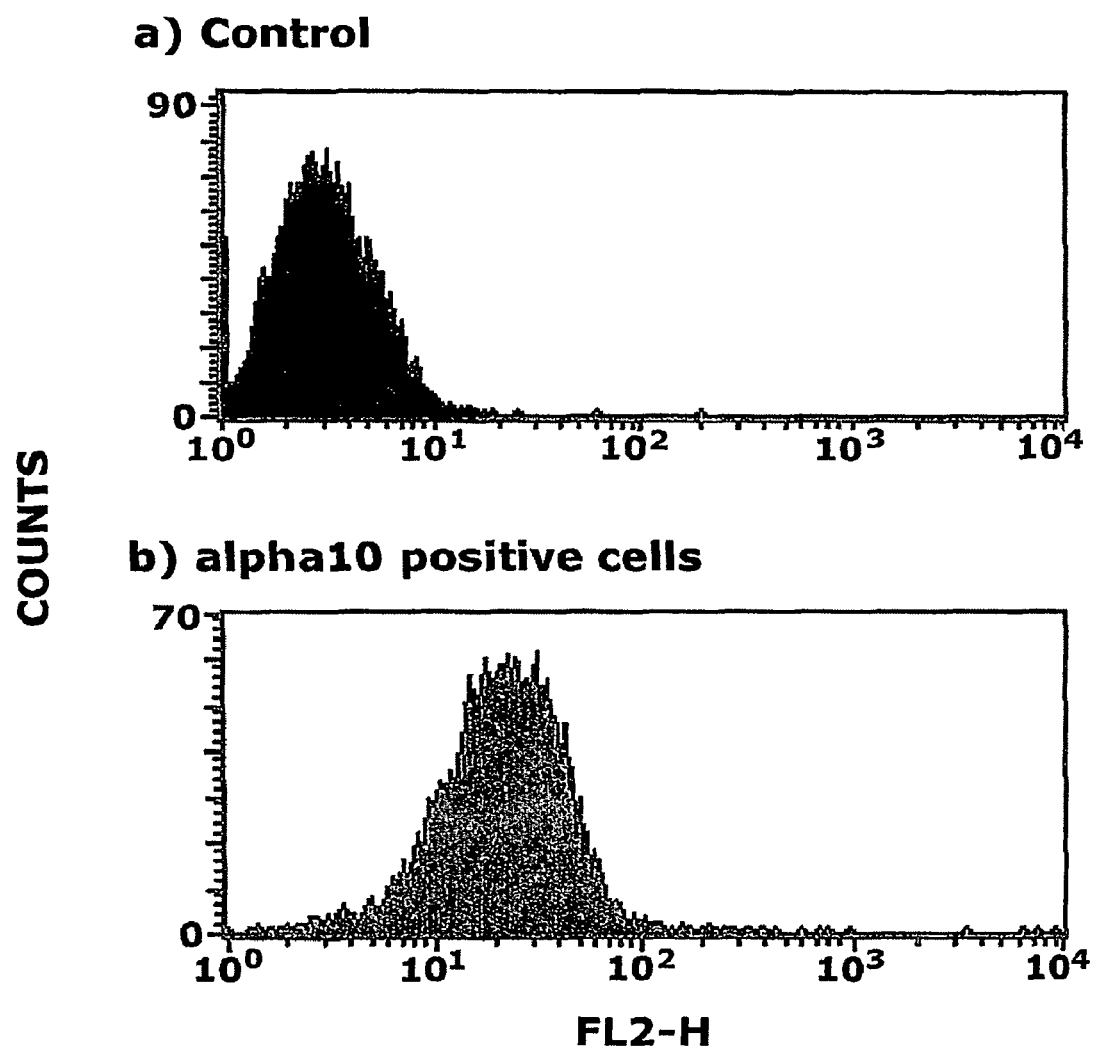

FIG. 4 shows flow cytometry histograms. After 2 weeks treatment with FGF-2, 96% of the cells treated with FGF-2 expressed the integrin alpha10 (lower panel, FIG. 4b). Control (secondary antibody alone) is shown in the upper panel in FIG. 4a.

DETAILED DESCRIPTION OF THE INVENTION

Definitions

As used herein, the terms "rodent" and "rodents" refer to all members of the phylogenetic order Rodentia.

The term "murine" refers to any and all members of the family Muridae, including rats and mice.

The term "substantially free from" is herein intended to mean below detection limits of the assay used thereby appearing negative, i.e. free from.

The term "committed" is herein intended to mean dedicated to, or focused on. Thus, a committed cell is a cell that is dedicated to, or focused on a specific differentiation pathway. From this it will follow that an uncommitted cell is not dedicated to, or focused on, any specific differentiation pathway and has several options.

Integrin Alpha10 and Integrin Alpha11 as a Marker for MSC

We have surprisingly found that the integrins alpha10beta1 and alpha11beta1 are present on human mesenchymal stem cells. Thus, these integrins can be used to identify, differentiate, and isolate mesenchymal stem cells from a mixed cell population and will be a useful tool in cell therapy to repair damaged tissue.

The human integrin alpha10 chain sequence is known and publicly available at GenBank™/EBI Data Bank accession number AF074015. Thus, new uses and methods of the integrin alpha10 chain are disclosed in the present invention.

The human integrin alpha11 chain sequence is known and publicly available at GenBank™/EBI Data Bank accession number AF137378. Thus, new uses and methods of the integrin alpha11 chain are disclosed in the present invention.

As revealed above, the present invention relates to a marker for mesenchymal stem cells (MSC), comprising an integrin alpha 10 chain and/or integrin alpha 11 chain expressed on the cell surface of mammalian MSC or intracellular in mammalian MSC.

In a further embodiment, the integrin alpha10 and/or integrin alpha 11 chain is expressed as a heterodimer in combination with an integrin beta1 chain.

Mammalian MSC is generally isolated from bone marrow, peripheral blood, cord blood, liver, bone, cartilage, perichondrium, muscle, periosteum, synovium or fat. The isolation may be based on the cells capacity to adhere to plastic culture dishes and form colonies under specific culture conditions, while the majority of bone marrow cells do not adhere and form colonies. Suitable protocol for isolation of mammalian MSC, without including the marker according to the invention, is further given in detail in Mason J M et al (2000, Cartilage and bone regeneration using gene-enhanced tissue engineering. Clin. Orthop. 379S:S171-178), Chu C R et al (1997, Osteochondral repair using perichondrial cells in Clin. Orthop. 340:220-229 (2000), and Dounchis J S et al (2000, Cartilage repair with autogenic perichondrium cell and polylactic acid grafts. Clin. Orthop. 377:248-264). Thus, known methods may be a used, but with the introduction of the marker(s) according to the invention.

The colonies may further be expanded and then induced with defined factors to differentiate into specific mesenchymal tissues. For chondrocytes, the culture is a culture in pelleted micromass or in alginate without serum, and with TGFbeta3 added as a defined factor. For osteogenic cells, cells may be cultured in the presence of dexamethasone, beta-glycerol phosphate, ascorbate, and 10% FBS (foetal bovine serum), and for adipocytes, cells may be cultured in the presence of 1-methyl-3-ispbutylxanthine, dexamethasone, insulin, and indomethacin.

Thus, the use of the marker(s) according to the invention in the isolation and expansion protocols will give a homogenous MSC population. Mesenchymal stem cells are not isolated and expanded this way are a homogenous population. More details concerning suitable factors to be included in cutures for expansion of specific MSC are given by Caplan, A I (1991, Mesenchymal Stem Cells. J. Orthop. Res. 9:641-650), Pittenger M F et al. (1999, Mutlilineage potential of adult human mesenchymal stem cells, Science. 284:143-7), and by Minguell J J, Erices, A and Conget, P (2001, Mesenchymal Stem Cells. Exp. Biol. Med. 226(6):507-520 —table of all factors that may be required to differentiate cells) all references are incorporated herein by reference.

Human MSC may be isolated from bone marrow, peripheral blood, cord blood, liver, bone, cartilage, perichondrium, muscle, periosteum, synovium or fat. The MSC may then further be isolated following a density centrifugation and found as a part of a mononuclear cell fraction layer at the density interface of 1.073 g/ml (Percoll™, Pharmacia). Suitable protocols are given in detail in Vogel W et al (2003, Heterogeneity among bone marrow-derived mesenchymal stem cells and neural progenitor cells) and by Nevo, Z et al (1998, The manipulated mesenchymal stem cells in regenerated skeletal tissues. Cell Transplant 7:63-70) both references incorporated herein by reference.

Out of this mononuclear cell fraction, $1/10\,000$-$1/100\,000$ cells form colonies upon culture in serum in culture dishes (Bruder S P et al (1997) Growth kinetics, self-renewal, and the osteogenic potential of purified human mesenchymal stem cells during extensive subcultivation and following cryopreservation. J. Cell. Biochem. 64:278-294).

Thus, including the marker according to the invention, comprising an integrin alpha 10 chain and/or integrin alpha 11 chain in known isolation and expansion protocols, as well as using the marker(s) alone, will be highly valuable for further evaluation and enrichment of the MSC population. Particularly, no other specific and unique marker as the marker according to the invention for mammalian MSC is known.

A Method for Identifying MSC

According to the invention, a method for identifying a mammalian MSC is disclosed. The method comprises the steps of
  a) providing a sample comprising MSC,
  b) detecting integrin chain alpha10 and/or alpha11 expression on the cell surface of a MSC or intracellular in MSC,
  c) scoring the integrin alpha10 and/or alpha11 chain expression, and d) identifying the MSC according to the scoring in c) above.

In more detail, the method according to the invention may further comprise the steps of:
e) providing a cell suspension comprising mammalian mesenchymal stem cells,
f) contacting the cell suspension in e) with a monoclonal antibody or fragments thereof binding to the integrin alpha10beta1/or alpha11beta1, under conditions wherein said monoclonal antibody or fragments thereof form an antibody-antigen complex with the extracellular domain of integrin alpha10beta1/alpha11beta1,
g) separating cells binding to said monoclonal antibody or fragments thereof in f), and optionally
h) recovering the cells binding to the monoclonal antibody or fragments thereof in g) from said antibody or fragments thereof, thereby producing a population of mammalian mesenchymal stem cells, optionally free from said antibody or fragments thereof.

The cell suspension provided in e) above, comprising mammalian MSCs may be isolated from bone marrow, peripheral blood, cord blood, liver, bone, cartilage, muscle, perichondrium, periosteum, synovial tissue, fat or any tissue comprising MSCs. The cell suspension may further be isolated from mammalian iliac crest, femora, tibiae, spine, rib or other medullary spaces. Other sources of human MSCs include embryonic yolk sac, placenta, and umbilical cord. If the population of cells is collected from BM, only 0.01-0.001% of the starting population, or "crude population", are MSCs. Though, this may vary between different donors.

In one further embodiment, the mammalian MSCs are human MSCs.

In one further embodiment, the mammalian MSCs are murine MSCs.

In one further embodiment, the culture above is a culture for 2-4 weeks.

In one embodiment, the method for isolating a population of MSCs further comprises the steps of
i) collecting bone marrow aspirate (5-30 ml) from a human patient into a syringe containing e.g. heparin to prevent clotting,
j) washing the marrow sample with e.g. Dulbecco's phosphate-buffered saline (DPBS) or any similar saline solution, and recovering the cells after centrifugation at 900 g, and repeating this procedure once more.
k) loading the cells onto 25 ml of Percoll of a density of 1.073 g/ml in a 50-ml conical tube and separating the cells by centrifugation at 1100 g for 30 min at 20° C.,
l) collecting the nucleated cells from the interface, diluting with two volumes of DPBS, and collecting by centrifugation at 900 g. Resuspending the cells counting the cells, and plating out the cells at the required density, suitable 200,000-cells/cm$^2$,
m) culturing the cells in Dulbecco's modified Eagle's medium (DMEM) or any other suitable medium (low glucose) containing 10% foetal bovine serum (FBS),
n) replacing the medium at 24 and 72 hours and every third or fourth day thereafter, and
o) subculturing the hMSCs that grow as symmetric colonies at 10 to 14 days by treatment with 0.05% trypsin and 0.53 mM EDTA for 5 min, rinsed from the substrate with serum-containing medium, collected by centrifugation at 800 g for 5 min, and seeded into fresh flasks at 5000 to 6000 cells/cm$^2$.

The separation of MSCs is a selection and isolation step for separating the identified MSCs. Various techniques known to the skilled artisan may be employed to separate the cells by initially removing cells dedicated to other lineages than MSCs.

If an antibody or fragments thereof is used it may be attached to a solid support to allow for a highly specific separation. The particular procedure for separation employed, e.g. centrifugation, mechanical separation, such as columns, membranes or magnetic separation, should maximize the viability of the fraction to be collected. Various techniques of different efficacy may be employed known to a person skilled in the art. The particular technique employed will depend upon efficiency of separation, cytotoxicity of the methodology, ease and speed of performance, and necessity for sophisticated equipment and/or technical skill.

Procedures for separation of MSCs from a cell suspension aided by the method according to the invention may include magnetic separation, using e.g. antibody-coated magnetic beads, affinity chromatography based on the antibody or fragments thereof according to the invention, and "panning" with an antibody or fragments thereof attached to a solid matrix, e.g., a plate, or other convenient techniques.

Techniques providing accurate separation include fluorescence activated cell sorters by the use of e.g. an antibody or fragments thereof in the method according to the invention, which can have varying degrees of sophistication, e.g., a plurality of colour channels, light scattering detecting channels, impedance channels, etc. known to the skilled man in the art.

In one embodiment, a first enrichment step of MSCs in the provided cell population is made. This first selection may be a negative selection of the MSCs, i.e. other lineage-committed cells are depleted, or removed, from the initial population of cells.

In still a further embodiment, the first enrichment is a positive selection of MSCs that may be repeated until the desired purity of the MSCs is achieved.

As described in the paragraph above the MSC may be isolated by plastic adhesion of a mixed cell population, followed by further optional expansion of the cells with defined factors to differentiate into different mesenchymal tissues. For chondrocytes, the culture may be a culture in pelleted micromass or in alginate with or without serum, and with TGFbeta3 added as a defined factor. For osteogenic cells, cells may be cultured in the presence of dexamethasone, beta-glycerol phosphate, ascorbate, and 10% FBS (foetal bovine serum), and for adipocytes, cells may be cultured in the presence of 1-methyl-3-ispbutylxanthine, dexamethasone, insulin, and indomethacin. More suitable factors are exemplified by Minguell J J, Erices, A and Conget, P (2001) in Mesenchymal Stem Cells. Exp. Biol. Med. 226(6):507-520 incorporated herein by reference.

In further embodiments of the invention, other less specific and non-unique mammalian MSC markers may be analysed in parallel with the marker according to the invention. Such other markers are SH-2, SH-3, CD29, CD44, CD71, CD90, CD106, CD120a, CD124, CD105, and Stro-1 that MSC may express. Though, these markers are not unique for mammalian MSC. Markers that do not express on MSC are CD14, CD34 and CD45 and their expression, or lack of expression, may in further embodiments also be evaluated in the method according to the invention.

In a further embodiment, the expression above is detected by detecting the integrin alpha10 and/or integrin alpha 11 protein expression.

The expression of alpha10/alpha 11 may in one embodiment be analysed by fluorescent cell sorting, by using e.g. a fluorescence activated cell sorter (FACS®) or any other methodology having high specificity. Multi-colour analyses may be employed with the FACS, which is particularly convenient. MSCs may, thus, be separated on the basis of the level of staining for the particular antigens.

In a first separation, antibodies for other markers may be used labelled with one or more fluorochrome(s). Other markers to be used may in further embodiments be SH-2, SH-3, CD29, CD44, CD71, CD90, CD106, CD120a, CD124, CD105, and Stro-1 that MSCs may express. Markers that are not expressed on MSCs are CD14, CD34 and CD45 and their expression, or lack of, may in further embodiments also be evaluated in the method according to the invention or a fragment.

If further lineages or cell populations not being MSCs are to be removed in one step, various antibodies to such lineage-specific markers may be included.

Fluorochromes, which may find use in a multi-colour analysis, include phycobiliproteins, e.g., phycoerythrin and allophycocyanins, fluorescein, Texas red, etc. well known to the skilled man in the art.

The MSCs may be selected against dead cells, by employing dyes associated with dead cells (propidium iodide, LDS). The cells may be collected in a medium comprising foetal calf serum.

MSCs may as well be selected based on light-scatter properties and their expression of various cell surface antigens, in combination with the identification using the method according to the invention.

Alternatively, MSCs may be analysed by immunoprecipitation thereby detecting and identifying integrin alpha10 and/or alpha11 chain expression. A suitable immunoprecipitation protocol is given in brief below. Any other suitable immunoprecipitation method may, of course, be used in the method according to the invention.

In brief,
1. Antibodies against the cytoplasmic domains of integrin subunits alpha10 and alpha11 can be used to specifically immunoprecipitate integrins alpha10beta1 and alpha11beta1 respectively from cell lysates. Polyclonal antibodies suitable for immunoprecipitation of integrin alpha10 or alpha11 are known and published in J. Biol. Chem. (1998, 273: 20383-9).
2. MSCs expressing either the integrin subunit alpha10 or alpha11 may then be grown in a suitable cell culture medium e.g. DMEM, IMEM, RPMI optionally with serum and growth factors. Cells adherent on the plate are washed once with PBS and then surface biotinylated using e.g. 0.5 mg/ml Sulfo-NHS-LC-biotin (Pierce) in 4 ml PBS for 20 min on ice or any other suitable biotinylation reagent known to a man skilled in the art.
3. Cells are then washed once with PBS and 10 ml 0.1M glycine/PBS were added for 5 min on ice. After washing once with PBS cells are lysed in 1 ml lysis buffer (1% NP-40, 10% glycerol, 20 mM Tris/HCl, 150 mM NaCl, 1 mM $MgCl_2$, 1 mM $CaCl_2$, protease inhibitor cocktail Roche, pH7.5) on ice.
4. The cell lysate is spun down at 15.000 g for 10 min and the supernatant removed and incubated with 1 µl of α10/α11 pre-immune serum and then 20 µl Prot G sepharose (Amersham) in 100 µl lysis buffer is added.
5. After rotating 1 h at 4° C. the lysate is centrifuged for 1 min at 8000 rpm and the supernatant is collected. For each subsequent immunoprecipitation 150 µl cell lysate supernatant is pipetted into an eppendorf tube and 1 µl of antiserum or monoclonal antibody solution is added.
6. Antibodies used are rabbit-anti-human α10 serum and for rabbit-anti-human α11 serum (both sera against the cytoplasmic domains of the integrins published by Tiger et al., (Developmental Biology (2001) 237:116) for alpha11 and by Camper et al (J. Biol. Chem. (2001) 306:107-116) for alpha10).
7. After 2 h rotating at 4° C., 20 µl prot G sepharose (Amersham) in 1000 lysis buffer is added and the mixture further rotated for another 45 min. The Sepharose-beads are then spun down briefly and washed three times with lysis buffer.
8. 20 µl SDS PAGE sample buffer (including 100 mM DTT) is added to the sepharose beads and the samples boiled for 5 min.
9. 5 µl of each sample is run on an 8% straight gel (Novex) and then electro-transferred onto a PVDF membrane. The membrane is blocked in 2% BSA/Tris buffer salin 0.05% Tween for 1 h, washed once with Tris buffer salin 0.05% Tween and then incubated with 2 µl Extravidin-peroxidase (Sigma) in 8 ml blocking buffer.

After 1 h the Extravidin-peroxidase solution is removed and the membrane washed 3×20 min in TBST. Surface biotinylated proteins can then be detected with e.g. ECL (Amersham) and visualised on a photographic film.

In still a further embodiment, the integrin chain alpha10 and/or alpha11 expression is detected on the cell surface of a MSC or intracellular in a MSC in the method according to the invention. Methods given above, e.g. flow cytometry and immunoprecipitation may be used.

In still a further embodiment, the expression in b) above is detected by any immunoassay, such as the methods described in Immunochemical protocols (Methods in molecular biology, Humana Press Inc). The detection may be performed by various methods, e.g. any immunomethod known to the skilled man in the art, such as immunoprecipitation, Western blotting or flow cytometry methods, e.g. fluorescence activated cell sorting (FACS). Antibodies, such as monoclonal antibodies or fragments thereof, are particularly useful for identifying markers, surface membrane proteins as well as intracellular markers, associated with particular cell lineages and/or stages of differentiation. Thus, it is suitable for the identification of integrin alpha10 as well as alpha11. Still, identification may as well be performed by any specific molecule, such as a protein or peptide, binding specifically to the integrin alpha10 and/or the integrin alpha11 molecule. Examples of such proteins or peptides are natural ligands, binding to the integrin alpha10 and/or the integrin alpha11 molecule. Such natural ligands may be made recombinant, chemically synthesised, or purified from a natural source. In still a further embodiment, the expression above is detected by detecting the integrin alpha10 and/or integrin alpha 11 mRNA expression. Detection of mRNA expression of a specific protein is well known to the skilled man in the art, and is generally done by probing the mRNA with a DNA or RNA probe specific for the mRNA of interest, under hybridisation conditions where the probe is not hybridising to other mRNA molecules. Different polymerase chain reactions (PCR) may also be used, which is obvious to the skilled man in the art.

A suitable PCR-method is given below. In brief, polymerase chain reaction (PCR) may be used.

RNA may be prepared from human mesenchymal stem cells or chondrogenic precursor cells by standard methods, for example by the use of RNeasy Mini Kit (Qiagen Germany).

cDNA may be produced by reverse transcriptase reaction, Superscript II (Invitrogen, USA) according to manufacturers recommendation with oligo d(T)-primers or gene specific primers.

PCR is thereafter performed to amplify the cDNA. Specific primers for α10, forward 5' GCT CCA GGA AGG CCC CAT TTG TG 3' (SEQ ID NO: 7) and reverse 5'GTG TTT TCT TGA AGG GTG CCA TTT 3' (SEQ ID NO: 8) or for α11, forward 5'GCT GCA GGC AGT GAC AGT A 3' (SEQ ID NO: 9) and reverse 5'GCG ATG GGA ATG GTG ATC T 3' (SEQ ID NO: 10) are added to the cDNA and the specific product is amplified by Platinum Taq DNA polymerase (Invitrogen, USA) according to their recommendations at 65° for 30 cycles.

The scoring of the integrin alpha10 and/or the integrin alpha11 molecule expression may be done relative to a reference cell population expressing the integrin alpha10 and/or the integrin alpha11 molecule, as well as to a cell population not expressing the integrin alpha10 and/or the integrin alpha11 molecule. Examples of cells expressing the integrin alpha10 and alpha11 are C2C12 cells, HEK293 cells transfected with alpha10 and alpha11 integrin sequences. Examples of cells not expressing alpha10 and alpha11 are non-transfected C2C12 cells and HEK293 cells.

A Method for Producing an Isolated Population of Cells Enriched for Mammalian MSC According to the invention, a method is disclosed for producing an isolated population of cells enriched for mammalian MSC relative to a reference population, the method comprising the steps of
 a) providing a at least a portion of a population of cells, or at least a portion of a reference population, comprising MSC and at least one cell other than a MSC,
 b) introducing into the population of cells in a) above a compound identifying the MSC,
 c) selecting and isolating from the population of cells in b) above the MSC, thereby producing a population of cells enriched for MSC.

Providing a population is described in the paragraphs above, and may be performed in a similar way as in the method for identification of MSC. If the population of cells is collected from BM, at about 0.01-0.001% of the starting population, or "crude population", is MSC. Though, this may vary between different donors.

The compound introduced to identify the MSC may be a protein, peptide, monoclonal antibody, or part thereof, or polyclonal antibody identifying the MSC. In one embodiment, the MSC is identified as a MSC by detecting expression of integrin chain alpha10 and/or alpha11 expression on the cell surface of said MSC according to the method for identifying MSC described above.

The selection and isolation of MSC is a separation step for separating, and thus isolating, the identified MSC. Various techniques may be employed to separate the cells by initially removing cells dedicated to other lineages than MSC. Monoclonal or polyclonal antibodies, or parts thereof, are particularly useful for identifying markers, here on intact viable cells, wherein the markers are surface membrane proteins associated with particular cell lineages and/or stages of differentiation. The compound used to identify the MSC may also be used for the separation step. Thus, said compound(s), such as antibodies, or parts thereof, may be attached to a solid support to allow for a first crude separation. Examples of solid supports are beads e.g. magnetic beads, agarose or other similar types of beads known to the skilled man in the art. Any means suitable for separation of cells may be employed on the condition that the separation is not unduly detrimental to the viability of a cell.

The separation techniques employed should maximize the retention of viability of the fraction to be collected. The assessment of viability is described below.

In brief, assessment of cell viability may be performed using e.g. flow cytometry. Thus, after staining cells, but before running on flow cytometer, the following amount/concentration of an appropriate cell viability dye can be added to discriminate between live/dead cells. A number of such dyes exist, of which examples and typical methods for using them are described. The principle is the same for most of these dyes: these dyes enter the cells if the cell membrane is compromised; as such, cells that stain with these dyes are dead, and cells that do not stain are considered live.

Examples of dyes are:
a) Propidium Iodide (PI):
Stock: 50 ug/uL in ethanol/PBS
Add: 1 uL per 100 uL of media in tube.
b) 7-Aminoactinomycin D (7 AAD)
Stock: 1 mg/mL in MeOH
Add: 1 uL per 100 uL of media in tube
c) To-Pro3
Stock: 1 mM in DMSO
Add: 1 uL per 500 uL to 1 mL of solution
d) Ethidium Monoazide (EMA)
Stock: 50 ug/mL in EtOH
Add: 5 ug/mL per $1 \times 10^6$ cells Other methods may be described in Flow Cytometry and Cell Sorting (Springer Lab Manual) by A. Radbruch Springer Verlag ($2^{nd}$ edition, January 2000)

The cell viability of the fraction collected is >90%, preferably 95, 96, 97, 98, 99, 99.9, or even 100%.

The particular technique employed for separation of cells in the method according to the invention will depend upon efficiency of separation, cytotoxicity of the methodology, ease and speed of performance, and necessity for sophisticated equipment and/or technical skill.

Procedures for separation may include magnetic separation, using e.g. antibody-coated magnetic beads, affinity chromatography, cytotoxic agents joined to a monoclonal antibody or used in conjunction with a monoclonal antibody, e.g., complement and cytotoxins, and "panning" with antibody attached to a solid matrix, e.g., a plate, or other convenient techniques. Techniques providing accurate separation include fluorescence activated cell sorters, which can have varying degrees of sophistication, e.g., a plurality of colour channels, light scattering detecting channels, impedance channels, etc. known to the skilled man in the art.

Further protocols for separation methods suitable to be used in the method according to the invention are described by Orfao, A and Ruiz-Arguelles, A ((1996) General Concepts about Cell Sorting Techniques. Clin Biochem. 29(1):5-9), and by Herzenberg, L A, De Rose, S C and Herzenberg, L A ((2000) Monoclonal Antibodies and FACS: complementary tools for immunobiology and medicine. Immunol. Today. 21(8):383-390).

In one embodiment of the method according to the invention, at least one enrichment step of mammalian MSC is included.

In still a further embodiment, the first enrichment step of MSC is a negative selection of the MSC, i.e. other lineage-committed cells are depleted, or removed, from the initial population of cells. Examples of such cells to be removed in the negative selection are identified by the following markers: CD14 (monocytes, granulocytes, dendritic cells, macrophages and B cells), CD34 (haematopoietic progenitor cells) and CD45 (leukocytes). These and other markers useful for negative selection of mammalian MSC are described in detail by Conget, P A, Minguell J J ((1999) Phenotypical and functional properties of human bone marrow mesenchymal progenitor cells. J. Cell Physiol. 181:67-73), and by Pittenger M F et al. ((1999) Mutlilineage potential of adult human mesenchymal stem cells. Science. 284:143-7) both references incorporated herein by reference.

In still a further embodiment, the first enrichment is a positive selection of MSC that may be repeated till the desired purity of the MSC is achieved. For a positive or a negative selection, proteins, peptides, monoclonal or polyclonal antibodies may be used as a compound to identify the integrin alpha10 or integrin alpha 11 molecule as described above. The compound may be conjugated with means for separation, such as magnetic beads, which allow for direct separation; biotin, which can be removed with avidin; or streptavidin bound to a support; fluorochromes, which can be used with a fluorescence activated cell sorter; or the like, to allow for ease of separation of the particular cell type as exemplified in the paragraphs above. Any technique may be employed which is not unduly detrimental to the viability of the cells of interest, i.e. the MSC.

In one embodiment, the selection is performed by fluorescent cell sorting, by using e.g. a fluorescence activated cell sorter such as a FACS®, or any other similar methodology having high specificity. Multi-colour analyses may be employed with the FACS which is particularly convenient and the technique well known to person skilled in the art of flow cytometry. The cells may be separated on the basis of the level of staining for the particular antigens. In a first separation, antibodies for other markers may be used labelled with one fluorochrome, while the antibodies for the dedicated lineages, i.e. the integrin alpha10 and/or integrin alpha11, may be conjugated to (a) different fluorochrome(s). Other markers may in further embodiments be SH-2, SH-3, CD29, CD44, CD71, CD90, CD106, CD120a, CD124, CD105, and Stro-1 that MSC may express. Markers that are not expressed on MSC are CD14, CD34 and CD45 and their expression, or lack of, may in further embodiments also be evaluated together with the marker according to the invention, e.g. integrin alpha10 and/or integrin alpha11 expression.

If further lineages or cell populations are to be removed in this step, various antibodies to such lineage specific markers may be included. Fluorochromes which may find use in a multi-colour analysis include phycobiliproteins, e.g., phycoerythrin and allophycocyanins, fluorescein, Texas red, etc. The cells may be selected against dead cells, by employing dyes associated with dead cells such as propidium iodide or LDS-751 (Laser Dye Styryl-751 (6-dimethylamino-2-[4-[4-(dimethylamino)phenyl]-1,3-butadienyl]-1-ethyl quinolinium perchlorate)). The cells may be collected in any suitable cell culturing media, such as Iscove's modified Dulbecco's medium (IMDM), or in any physiological saline solution, preferably buffered, such as phosphate buffer saline (PBS), optionally with foetal calf serum (FCS) or bovine serum albumin (BSA) present. Other techniques for positive or negative selection may be employed, which permit accurate separation, such as affinity columns, and the like, further described by Silvestri F, Wunder E, Sovalat H, Henon P, Serke S in Positive selection of CD34+ cells: a short review of the immunoadsorption methods currently available for experimental and clinical use(Report on the "2nd European Workshop on stem Cell Methodology", Mulhouse, France, May 3-7, 1993. J. Hematother. 1993 Winter; 2(4):473-81) and by Basch R S, Berman J W, Lakow E. in Cell separation using positive immunoselective techniques (J Immunol Methods. 1983 Feb. 11;56(3):269-80).

Cells may be selected based on light-scatter properties as well as their expression of various cell surface antigens.

While it is believed that the particular order of separation is not critical to this invention, the order indicated is one way of performing the invention that is known to work. Thus, suggestively, cells are initially separated by a crude separation, preferably a negative selection removing cells not committed for MSC using negative cell markers such as CD14, CD34 and CD45. Such cells are negative for the expression of integrin alpha10 and/or alpha11. The negative selection is followed by a fine separation, which is a positive selection, wherein the positive selection is of a marker associated with MSC and negative selection for markers associated with lineage committed cells, and other stem cell populations not being MSC. This separation is then followed by selection for a cellular population, or a cellular composition comprising said population, having multi-lineage potential as a MSC and enhanced self-regeneration capability. The composition is further described below.

Isolated Mammalian MSC

According to the invention, an enriched cellular population of mammalian MSC is disclosed. Such a cellular population comprises intact, viable MSC, wherein the MSC are characterised by
  a) expressing an integrin alpha 10 chain and/or integrin alpha 11 chain on the cell surface of said MSC or intracellular in MSC,
  b) being substantially free from expression of molecules specific for committed haematopoietic cells.

Molecules specific for committed haematopoietic cells are e.g. CD45. Other molecules the MSC cells are substantially free from are e.g. CD34 and CD14.

In further embodiments, the enrichment of such a population is about 70, 80, 90, 95, 98, 99, 99.9, or even 100%. The viability of such cells is discussed in detail above.

According to the invention an isolated MSC expressing a marker according to the invention is disclosed. The isolated MSC are obtainable by the method for producing a population of cells enriched for MSC according to the invention.

A Cellular Composition

According to the invention, a mammalian cellular composition is disclosed. Such a composition comprises the enriched mammalian cellular population according to the invention, or the isolated mammalian MSC according to the invention.

Compositions having greater than 90%, usually greater than about 95%, such as 97, 98, 99.9%, of human MSC cells may be achieved according to the disclosed methods for enrichment of MSC. Such MSC are able to provide for cell regeneration and development of members of all of the various lineages of MSC, such as osteocytes, chondrocytes, e.g. hypertrophic chondrocytes, muscle cells, myotubes, stromal cells, T/L fibroblasts, adipocytes, tenocytes, dermal cells and other cells. This is generally done in cultures, supplied with specific factors described earlier.

Ultimately, a single cell may be obtained from a MSC composition and used for long-term reconstitution of a mammal deficient for MSC and/or mesenchymal tissue formation or regeneration. The MSC composition should be administered in a therapeutic effective dosage, wherein the dosage is a specific cell number able to repopulate said mammal, such as a human being. This cell number may be different from donor to donor and may be determined empirically form case to case by a person skilled in the art of cell transplantation of cells to mammals, such as a human being, in the need thereof.

Various procedures can be contemplated for transferring and immobilising the MSCs, and the composition comprising MSC, including injecting the isolated cells into the site of skeletal defect e.g. damage to articular cartilage, incubating isolated cells in suitable gel and implanting, incubating with bioresorbable scaffold, or by systemically infusing etc. Different procedures are known and described in detail by e.g. Risbud, M V and Sittenger M ((2002) Tissue Engineering: advances in in vitro cartilage regeneration. Trends in Biotech. 20(8):351-356), by Caplan, A. and Bruder, S. P. ((2001) Mesenchymal stem cells: building blocks for molecular medicine in the 21st century. Trends Mol. Med. 7(6):259-64), by Lazarus, H M et al ((1995) Ex vivo expansion and subsequent infusion of human bone marrow-derived stromal progenitor cells (mesenchymal progenitor cells): Implications for therapeutic use. Bone Marrow Transplant 16:557-564), and by Koc O N et al ((2000) Rapid hematopoietic recovery after coinfusion of autologous-blood stem cells and culture-expanded marrow mesenchymal stem cells in advanced breast cancer patients receiving high-dose chemotherapy. J. Clin. Oncol 18(2):307-16).

Optionally MSCs can be incubated with an antibody to the integrin alpha10 or alpha11 in order to hold the cells in place. Thus antibodies can be conjugated to a bioresorbable scaffold allowing immobilisation of the cells before implantation into the damaged or defect site, e.g. into the site of a skeletal defect. The scaffold allows 3D immobilization of MSCs. Suitable biomaterial scaffolds are exemplified below. The examples given are not limiting the use of other suitable scaffolds obvious to a skilled artisan to choose if more suitable for the particular application.

Types of scaffold include, bioresorbable poly(α-hydroxy esters) scaffolds such as polylactic acid (PLLA), polyglycolic acid (PGA) and copolymer (PLGA).

Further embodiments include scaffolds derived from polymeric gels such as hyaluronic acid, collagen, alginate and chitosan.

Further embodiments include scaffolds derived from porous carriers, such as tricalcium phosphate and/or hydroxyapatite ceramic block (Luyten, F. P, Dell'Accio, F and De Bari, C (2001) Skeletal tissue engineering: opportunities and challenges. Best Prac & Res. Clin. Rheum. 15(5): 759-770.)

The cellular composition according to the invention may be used for treatment of genetic diseases. Genetic diseases associated with MSC may be treated by genetic modification of autologous or allogeneic MSC to correct the genetic defect. For example, diseases such as different connective tissue diseases, e.g. osteogenesis imperfecta, Ehlers Danlos syndrome, Chondrodysplasia, Alport syndrome may be corrected by introduction of a wild-type gene into the MSC, either by homologous or random recombination. Methods for homologous recombination for correction of diseases are known and described by Hatada S, Nikkuni K, Bentley S A, Kirby S, Smithies O.((2000) Gene correction in hematopoietic progenitor cells by homologous recombination. Proc Natl Acad Sci USA 97(25):13807-11).

With allogeneic MSC, normal cells form a mammal of the same species lacking the genetic defect can be used as a therapy. Other embodiments of gene therapy may be introduction of drug resistance genes to enable normal MSC to have an advantage and be subject to selective pressure, e.g. the multiple drug resistance gene (MDR). More details are given in Aran J M, Pastan I, Gottesman M M (1999) Therapeutic strategies involving the multidrug resistance phenotype: the MDR1 gene as target, chemoprotectant, and selectable marker in gene therapy. (Adv Pharmacol 46:1-42).

Diseases other than those associated with MSC may also be treated, where the disease is related to the lack of a particular secreted product such as a hormone, enzyme, interferon, factor, or the like. By employing an appropriate regulatory initiation region, inducible production of the deficient protein may be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly connective tissue Modulation of MSC According to the invention a method for determining whether a test compound modulates a mammalian MSC differentiation is disclosed. Such a method comprises the steps of
 a) providing a MSC
 b) contacting the MSC with a test compound, and
 c) detecting a change in rate or pattern of differentiation of the MSC as an indication that the test compound modulates MSC differentiation.

The MSC provided may be an enriched cell population achieved according to any of the methods disclosed, the isolated MSC according to the invention, or the cellular composition according to the invention.

The test compound may be any compound known to affect or suspected to affect MSC, e.g. pharmaceutical compositions, drugs, polyclonal or monoclonal antibodies, or parts thereof, such as antibodies binding to integrin alpha10 and/or integrin alpha11 or any other molecule on the MSC, factors used to promote growth of MSC, e.g. FGF or foeatal bovine serum (FBS), or factors used to promote differentiation of MSC, e.g. dexamethasone, TGFbeta, insulin.

The detection of a change in rate or pattern of e.g. differentiation of the MSC as an indication that the test compound modulates MSC differentiation may be done via flow cytometry or any other suitable method, such as any immunomethod, known to a person skilled in the art. The change in rate or pattern of differentiation may be kinetic, functional or phenotypical studies of the MSC modulated with the test compound, relative for an untreated, or mock treated, MSC population. It may also be a comparison relative to least one second test compound.

In a further embodiment the MSC is identified as a MSC by detecting expression of integrin chain alpha10 and/or alpha11 expression on the cell surface of said MSC or intracellular in MSC according to the method of identifying MSC disclosed herein.

Use of the Mammalian MSC

The mammalian MSC, such as human or mouse MSC, provided herein find a number of uses. For instance, 1) regeneration of a host deficient in MSC; 2) treatment of a host by the re-engraftment of MSC for re-generation of bone, cartilage, muscle, marrow, tendon/ligament and connective tissue in a patient in the need thereof; 3) in detecting and evaluating growth factors relevant to MSC self re-generation; 4) in development of MSC lineages and screening for factors associated with their development and differentiation.

Further, the integrin alpha10 and/or alpha11 have several uses. Examples of uses may thus be to identify, differentiate, and isolate mammalian mesenchymal stem cells from a mixed cell population as useful tools in cell therapy to repair damaged tissue.

According to the invention, use of the integrin alpha10 and/or alpha11 according to the invention is disclosed for identification of MSC.

Further, a use of the integrin alpha10 and/or alpha11 according to the invention is disclosed, for modulating differentiation of a MSC.

Still even further, a use of the integrin alpha10 and/or alpha11 according to the invention is disclosed, for isolating a MSC or an enriched population of MSC.

Mammalian MSC

In the methods and uses disclosed in the present invention, mammalian MSC, mammalian cellular populations and mammalian cellular compositions are disclosed.

In specific embodiments, the mammal may be a human.

Still further embodiments include wherein the mammal is a rodent, such as a rat, mouse, or any other member of the family Muridae.

EXAMPLES

Example 1

Detection of Integrin Alpha10 and Integrin Alpha11 Chain on Human MSC

Objective

The objective of this example is to analyse human MSC for the expression of integrin alpha10 and alpha11, using immunoprecipitation.

Materials and Methods

Human mesenchymal stem cells (obtained from In Vitro, Sweden, at passage 2), were cultured in MSCBM medium (provided by In Vitro, Sweden) until passage 4 and then surface biotinylated.

In brief, cells adherent on the plate were washed once with PBS and then surface biotinylated using 0.5 mg/ml Sulfo-NHS-LC-biotin (Pierce) in 4 ml PBS for 20 min. Cells were then washed once with PBS and 10 ml 0.1M glycine/PBS were added for 5 min.

After washing once with PBS cells were lysed in 1 ml lysis buffer (1% NP40, 10% glycerol, 20 mM Tris/HCl, 150 mM NaCl, 1 mM $MgCl_2$, 1 mM $CaCl_2$, protease inhibitor cocktail BM, pH7.5). The cell lysate was collected with a plastic scraper, pipetted into an eppendorf tube and spun down for 10 min at 15.000 g.

The supernatant collected from the centrifugation step above was incubated with 2 microliter of alpha10 pre-immune serum followed by addition of 20 µl Prot G sepharose (Amersham) in 100 µl lysis buffer.

After rotating the cells in lysis buffer over night at 4° C. the lysate was centrifuged for 1 min at 8000 rpm and the supernatant collected. For each subsequent immunoprecipitation 150 µl cell lysate were pipetted into an eppendorf tube and 1 µl of antiserum was added. The sera used were rabbit-anti-human a10 and rabbit-anti-human a11, respectively (both sera against the cytoplasmic domains of the integrins).

After 1 h rotating at 4° C., 20 µl protein G Sepharose (Amersham) in 100 µl lysis buffer was added and the mixture further rotated for another 30 min. The Sepharose-beads were then spun down briefly and washed three times with lysis buffer.

20 µl SDS-PAGE sample buffer (including 100 mM DTT) was added to the Sepharose beads and then the samples were boiled for 5 min. 5 µl of each sample were run on a 8% SDS-PAGE gel (Novex) and then electro-transferred onto a PVDF membrane.

The membrane was blocked in 2% BSA/TBST (TBST: 20 mM Tris/HCl pH 7.5, 150 mM NaCl, 0.05% Tween 20) for 1 h, washed once with TBST and then incubated with 2 µl Extravidin-peroxidase (Sigma) in 8 ml blocking buffer.

After 1 h the Extravidin-peroxidase solution was removed and the membrane washed 3×20 min in TBST. Surface biotinylated proteins were then detected with ECL (Amersham) and visualised on a photographic film.

Results and Discussion

In FIG. 2, the result of the immunoprecipitation is shown. Human mesenchymal stem cells in culture express both integrins alpha10 and alpha11 on their surface. In the figure, the upper band is alpha10 (in the left lane) and alpha11 (in the right lane). The lower band in both lanes represents the beta1 chain. Both integrin alpha10 and alpha11 expression is identified.

Example 2

Identification of HEK293 Cells Expressing the Integrin Alpha10Beta1 and the alpha11beta1

Objective

The objective with this example is to use antibodies to alpha10 and alpha11 to identify and differentiate between HEK293 cells expressing the integrin alpha10beta1 and the integrin alpha11beta1.

Materials and Methods

Integrin alpha10 and alpha11-transfected HEK293 cells and non-transfected HEK293 cells were trypsinized, washed with PBS and then incubated for 20 min with integrin antibodies against alpha10 and alpha11 (1 µg/ml in PBS supplemented with 1% BSA).

Labelled cells were washed twice with PBS/1% BSA and then incubated for 20 min with PE labelled goat-anti-mouse Ig (Pharmingen, BD Biosciences) at a concentration of 1 µg/ml in PBS/1% BSA.

Cells were thereafter washed twice in PBS/1% BSA and were analysed on a FACSort® (Becton-Dickinson) by collecting 10,000 events with the Cell Quest® software program (Becton-Dickinson).

Results

The results are shown in FIG. 3A-I as histograms after FACS-analysis.

In FACS assay, the antibody against alpha10 bound to the HEK293 cells transfected with human alpha10 integrin-subunit, shown in FIG. 3E. This was seen as a displacement in the FACS histogram to the right.

The antibody against alpha10 did not bind to HEK293 cells transfected with human alpha11 integrin-subunit, as shown in the middle panel (right, FIG. 3F), or untransfected HEK293 cells, as shown in FIG. 3D).

Similarly, the antibody against alpha11 bound to the HEK293 cells transfected with human alpha11 integrin-subunit, shown in FIG. 3I. This was seen as a displacement in the FACS histogram to the right. The antibody against alpha11 did not bind to HEK293 cells transfected with human alpha10 integrin-subunit, as shown in FIG. 3H, or untransfected HEK293 cells, as shown in FIG. 3G).

FIG. 3A-C represent control (secondary antibody alone), which did not bind to any of the HEK293 cells tested.

In summary FIG. 3A-I shows that HEK293cells expressing the integrin alpha10beta1 and integrin alpha11beta1 can be specifically sorted by FACS analysis using antibodies directed against these integrins.

Example 3

Identification of MSC Expressing the Integrin Alpha10 from Human Colonyforming Cells Derived from Human Bone Marrow Objective To test whether colony-forming cells derived from human bone marrow express the integrin alpha10 and represent a population of mesenchymal stem cells.

Materials and Methods

Human mononuclear bone marrow cells were isolated from bone marrow by density centrifugation.

30×10⁶ cells were taken in 20 ml medium (MSCGM medium provided by Poietics and delivered via Invitro, comprising 440 ml MSCBM (lot 017190) and 2×25 ml MCGS (lot 082295) and L-glutamine and Penicillin/Streptomycin) into a T75 flask and incubated in the cell incubator.

Cells were grown until day 12 (medium was changed twice) and then trypsinized and split (5000 cells/cm²). In general, cells were split at 90% confluency.

Cells were grown for a further 3 days and then split again (5000 cells/cm²). At this point the influence of FGF-2 on alpha10-expression on hMSC was investigated: One plate was grown in medium as before and one plate was grown in medium+5 ng/ml FGF-2. After two weeks in culture with or without FGF-2 (including one passage) the cells were analysed by FACS using a monoclonal antibody to alpha10 as a means to analyse the cells.

Results

The results are shown in FIG. 4 as flow cytometry histograms.

After 2 weeks treatment with FGF-2, 96% of the cells treated with FGF-2 expressed the integrin alpha10 (lower panel, FIG. 4b).

Control (secondary antibody alone) is shown in the upper panel in FIG. 4a. Cells were tested for non MSC markers (CD34 and CD45) and found to be negative (results not shown).

Cells were also analysed for their morphology and light microscopy revealed that the cells formed colonies typical of MSCs.

---

The invention claimed is:

1. A method for producing an isolated population of mammalian cells enriched for mesenchymal stem cells relative to a reference population, the method comprising the steps of
   a) providing at least a portion of a population of cells, or a portion of a reference population, comprising at least one mesenchymal stem cell and at least one cell other than a mesenchymal stem cell,
   b) introducing into the population of cells in a) above an antibody or fragment thereof identifying an integrin alpha 10 chain expressed on the cell surface of mesenchymal stem cells,
   c) selecting and isolating from the population of cells in b) above the mesenchymal stem cell(s) expressing integrin alpha 10 chain, thereby producing a population of cells enriched for mesenchymal stem cells.

2. The method according to claim 1, wherein the mesenchymal stem cells are identified as mesenchymal stem cells by detecting expression of integrin alpha 10 chain on the cell surface of said mesenchymal stem cells.

3. The method according to claim 1, wherein the selection in c) above is performed by fluorescent cell sorting.

4. A method for isolating mammalian mesenchymal stem cells comprising the steps of
   a) providing a cell suspension comprising mammalian mesenchymal stem cells and at least one cell other than a mesenchymal stem cell,
   b) contacting the cell suspension with an antibody or fragments thereof binding to integrin alpha10 chain expressed on the cell surface of mesenchymal stem cells,
   c) separating cells binding to said antibody or fragments thereof in b), and optionally
   d) recovering the cells binding to the antibody or fragments thereof in c) from said antibody or fragments thereof, thereby producing a population of isolated mammalian mesenchymal stem cells, optionally free from said antibody or fragments thereof.

5. The method of claim 1, wherein the selection in c) above is performed using a solid support.

* * * * *